US006201111B1

(12) United States Patent
Brichard et al.

(10) Patent No.: US 6,201,111 B1
(45) Date of Patent: *Mar. 13, 2001

(54) METHODS FOR TREATING SUBJECTS WITH DISORDERS CHARACTERIZED BY EXPRESSION OF TUMOR REJECTION ANTIGEN PRECURSORS

(75) Inventors: Vincent Brichard; Aline Van Pel, both of Brussels (BE); Catia Traversari, Milan (IT); Thomas Wölfel, Mainz (DE); Pierre Coulie, Brussels (BE); Thierry Boon-Falleur, Brussels (BE); Etienne De Plaen, Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/224,834

(22) Filed: Jan. 4, 1999

Related U.S. Application Data

(60) Division of application No. 08/370,319, filed on Jan. 10, 1995, now Pat. No. 5,856,091, and a continuation-in-part of application No. 08/272,351, filed on Jul. 8, 1994, now abandoned, which is a continuation-in-part of application No. 08/032,978, filed on Mar. 18, 1993, now Pat. No. 5,620,886.

(51) Int. Cl.[7] ................................................. C07H 21/02
(52) U.S. Cl. ........................................ 536/23.1; 536/23.5
(58) Field of Search .................................. 536/23.1, 23.5

(56) References Cited

U.S. PATENT DOCUMENTS

| | | |
|---|---|---|
| 5,487,974 | 1/1996 | Boon-Falleur et al. . |
| 5,620,886 | 4/1997 | Brichard et al. .................... 435/240.2 |
| 5,856,091 * | 11/1999 | Brichard et al. ........................... 435/6 |
| 5,874,560 * | 2/1999 | Kawakami et al. ................. 536/23.5 |
| 5,994,523 * | 11/1999 | Kawakami et al. ................. 536/23.5 |

OTHER PUBLICATIONS

Kawakami, et al., "Cloning of the Gene Coding For A Shared Melanona Antigen Recognized by Autologous T. Cells Infiltrating Into Tumor", Proc. Natl. Acad. Sci., USA91:3515–3519 (Apr. 1994).

Traversari et al., "A Nonapeptide Encoded by Human Gene MAGE–1 Is Recognized on HLA–A1 by Cytolytic T Lymphocytes Directed Against Tumor MZ2–E" J. Exp. Med. 176: 1453–1457 (Nov. 1992).

Van der Bruggen et al., "A Gene Encoding an Antigen Recognized by Cytolytic T. Lymphocytes on a Human Melanoma", Science 254: 1643–1647 (Dec. 13, 1991).

Giebel, et al., "Organization and Nucleotide Sequences of the Human Tyrosinase Gene and a Truncated Tyroinase–Related Segment" (1991).

Van de Eynde et al., "Prescence on a Human Melanoma of Multiple Antigens Recognized by Autologous CTL", Int. J. Cancer 44:634–640 (1989).

Bodmer et al., "Anti–HLA–A2 antibody–enhancement of peptide association with HLA–A as detected by cytotoxic T. Lymphocytes", Nature 342: 443–446 (Nov. 23, 1989).

Wölfel et al., "Lysis of Human melanoma Cells by Autologous Cytolytic T Cell Clones", J. Exp. Med. 170: 797–810 (Sep. 1989).

Knuth et al., "Cytolytic T–cell clones against an autologous human melanoma: specificity study and definition of three antigens by immunoselection", Proc. Natl., Acad. Sci USA 86:2804–2808 (Apr. 1989).

Kwon, et al., "Isolation and Sequence of a cDNA clone for human tyrosinase that maps out the mouse C–albino locus," Proc. Natl, Acad. Sci USA 84:7473–7477 (1987).

Kawakami, et al., "Cloning of the Gene Coding For A shared Human Melanoma Antigen Recognized by Autologous T Cells Infiltrating into Tumor", Proc. Natl. Acad. Sci. USA 91: 3515–3519 (Apr. 1994).

* cited by examiner

Primary Examiner—Sheela Huff
(74) Attorney, Agent, or Firm—Fulbright & Jaworski, LLP

(57) ABSTRACT

The invention relates to nucleic acid molecules coding for a tumor rejection antigen precursor. Specifically, the tumor rejection antigen precursor, or 'TRAP', is processed into at least one tumor rejection antigen, which is presented by HLA-A2 molecules. Ramifications of the discovery are also set forth.

1 Claim, 6 Drawing Sheets

FIG. 4

| NORMAL TISSUES | As |
|---|---|
| melanocytes SK | + |
| heart | − |
| liver | − |
| kidney BA4 | − |
| prostate Clontech | − |
| adrenals | − |
| adrenals | − |
| adrenals | − |
| adrenals pool Clontech | − |
| testis Clontech | − |
| testis LB451 | − |
| brain Clontech | − |
| fetal brain Clontech | − |
| lung LB175 | − |
| lung LB195 | − |
| skin LB 177 | − |
| CTL SK29 IVS B | − |

MELANOMA

| CELL LINES | | TUMOR SAMPLES | |
|---|---|---|---|
| LB24-MEL | + | LB239-MEL | + |
| SK23-MEL | + | LB15-MEL | + |
| LE518-MEL | + | LB492-MEL | + |
| LB38-MEL | + | LB503-MEL | + |
| MZ13-MEL | − | LB435-MEL | + |
| LB33-MEL | − | LB224-MEL | + |
| LB3-MEL | + | LG18-MEL | + |

| OTHER TUMOR CELL LINES | |
|---|---|
| LB23 sarcoma | − |
| LE89.15 kidney tumor | − |
| BT20 breast caroinoma | − |
| LB63 colon carcinoma | − |
| T cell leukemia | − |

METHODS FOR TREATING SUBJECTS WITH DISORDERS CHARACTERIZED BY EXPRESSION OF TUMOR REJECTION ANTIGEN PRECURSORS

RELATED APPLICATIONS

This application is a divisional of Ser. No. 08/370,319 filed Jan. 10, 1995, now U.S. Pat. No. 5,856,091, and is a continuation-in-part of Ser. No. 08/272,351, filed Jul. 8, 1994, now abandoned which is a continuation-in-part of patent application Ser. No. 08/032,978 filed Mar. 18, 1993, now U.S. Pat. No. 5,620,886.

FIELD OF THE INVENTION

This invention relates to a nucleic acid molecule which codes for a tumor rejection antigen precursor. More particularly, the invention concerns a gene, whose tumor rejection antigen precursor is processed, inter alia, into at least one tumor rejection antigen that is presented by HLA-A2 molecules on cell surfaces.

BACKGROUND AND PRIOR ART

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., Advanced Immunology (J. P. Lipincott Company, 1987), especially chapters 6–10. The interaction of T cell and complexes of HLA/pep tide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Recently, much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes. Also see U.S. Pat. No. 5,342,774, incorporated by reference.

In U.S. patent application Ser. No. 938,334, now U.S. Pat. No. 5,405,940 the disclosure of which is incorporated by reference, nonapeptides are taught which are presented by the HLA-A1 molecule. The reference teaches that, given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 008,446, filed Jan. 22, 1993 and incorporated by reference, the fact that the MAGE-1 expression product is processed to a second TRA is disclosed. This second TRA is presented by HLA-C*1601-molecules. The disclosure shows that a given TRAP can yield a plurality of TRAs.

In U.S. patent application Ser. No. 994,928, filed Dec. 22, 1992, and incorporated by reference herein, tyrosinase is described as a tumor rejection antigen precursor. This reference discloses that a molecule which is produced by some normal cells (e.g., melanocytes), is processed in tumor cells to yield a tumor rejection antigen that is presented by HLA-A2 molecules.

U.S. patent application Ser. No. 32,978 cited supra, reports on a nucleic acid molecule which codes for a tumor rejection antigen precursor which differs from those described previously. The TRAP of the invention described therein is processed to at least one tumor rejection antigen that is presented by HLA-A2 molecules; however sequence analysis indicated that the TRAP of the invention is not, nor is it related to, tyrosinase. Thus the invention of the parent application relates to a nucleic acid molecule which codes for a tumor rejection antigen precursor, or "TRAP" molecule. This "TRAP" molecule is not tyrosinase. Further, the TRAP of the invention of the parent application is processed to at least one tumor rejection antigen, or "TRA", which is presented by HLA-A2 molecules. The TRA is not tyrosinase related, and other TRAs derived from the TRAPs of the invention may be presented by other HLA molecules.

In a paper published after the above-identified parent application, Kawakami, et al., Proc. Natl. Acad. Sci. USA 91: 3513–3519 (1994) also identified the subject matter of the parent application as a gene coding for a melanoma antigen.

Further work shows that the gene coding for this TRAP, referred to hereafter as "Melan-A", is about 18 kilobases long, and comprises 5 exons. It appears to be expressed only in melanoma and melanocytes, thus serving as a marker for these cells.

The invention and various aspects thereof will be elaborated upon in the disclosure which follows.

BRIEF DESCRIPTION OF THE FIGURES

FIG. 4 presents a panel of tissues, cell lines and tumors tested for expression of the Melan A gene, "AaGlcl24" via polymerase chain reaction (PCR) using oligonucleotide probes derived from the nucleic acid molecule described herein.

DETAILED DESCRIPTION OF PREFERRED EMBODIMENTS

EXAMPLE 1

A melanoma cell line, "LB-39-MEL" was established from melanoma cells taken from patient LB39, using standard methodologies. Once the cell line was established, a sample thereof was irradiated, so as to render it non-proliferative. These irradiated cells were then used to isolate cytolytic T cells ("CTLs") specific thereto.

A sample of peripheral blood mononuclear cells ("PBMCs") was taken from patient LB39, and contacted to the irradiated melanoma cells. The mixture was observed for lysis of the melanoma cells, which indicated that CTLs specific for a complex of peptide and HLA molecule presented by the melanoma cells were present in the sample.

The lysis assay employed was a chromium release assay following Herin et al., Int. J. Cancer 39:390–396 (1987), the disclosure of which is incorporated by reference. The assay, however, is described herein. The target melanoma cells were grown in vitro, and then resuspended at $10^7$ cells/ml in DMEM, supplemented with 10 mM HEPES and 30% FCS, and incubated for 45 minutes at 37° C. with 200 $\mu$Ci/ml of Na($^{51}$Cr)O$_4$. Labelled cells were washed three times with DMEM, supplemented with 10 mM Hepes. These were then resuspended in DMEM supplemented with 10 mM Hepes and 10% FCS, after which 100 ul aliquots containing $10^3$ cells, were distributed into 96 well microplates. Samples of PBLs were added in 100 ul of the same medium, and assays were carried out in duplicate. Plates were centrifuged for 4 minutes at 100 g, and incubated for four hours at 37° C. in an 80% CO$_2$ atmosphere.

Plates were centrifuged again, and 100 ul aliquots of supernatant were collected and counted. Percentage of $^{51}$Cr release was calculated as follows:

$$\% \ ^{51}\text{Cr release} = \frac{(ER - SR)}{(MR - SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL activity were expanded and cloned via limiting dilution, and were screened again, using the same methodology. The CTL clone LB39-CTL I/95 was thus isolated.

Figure 1C:
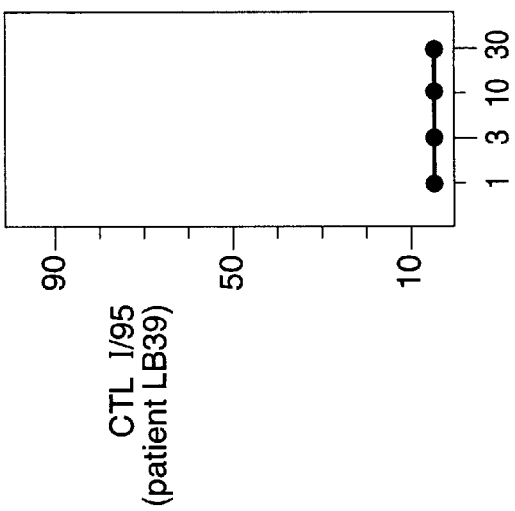
FIG. 1A presents results of cell lysis experiments using CTL clone I/95 against LB39-MEL, K562, and LB39 blasts.
FIG. 1B shows lysis using CTL clone I/95 against SK23-MEL and SK29-MEL.
Figure 1B:
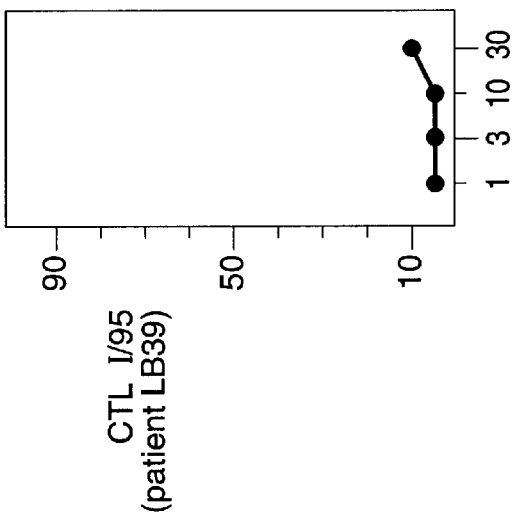
Figure 1A:
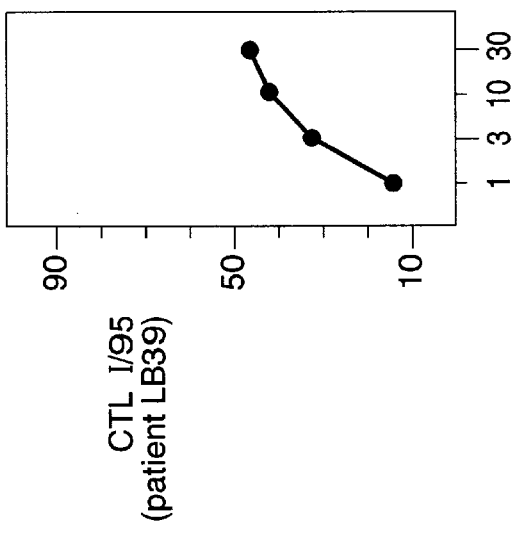
Figure 1E:
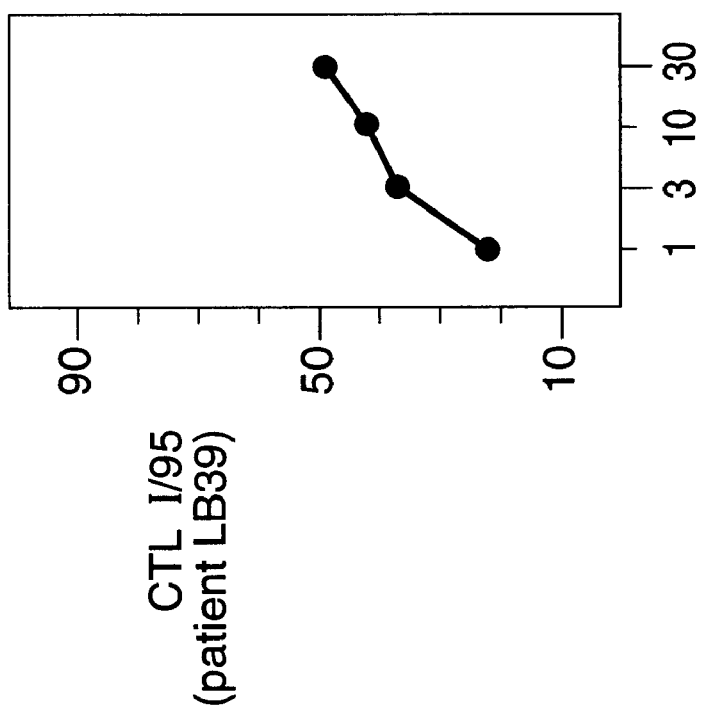
Figure 1D:
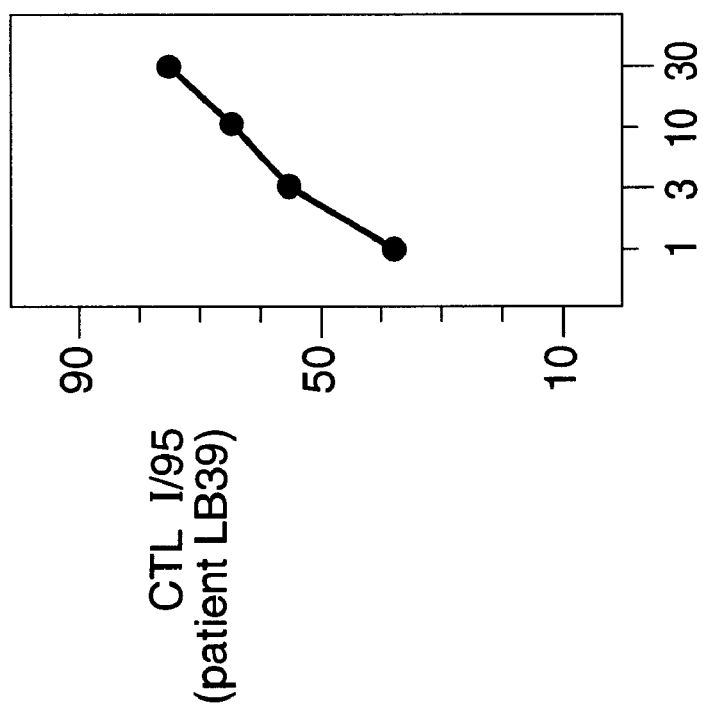

The same method was used to test target K562 cells, as well as autologous, PHA induced T cell blasts. These results, presented in FIG. 1A, show that this CTL clone recognizes and lyses the melanoma cell line, but neither of K562 or the T cell blasts. The CTL, LB39-CTL I/95, was then tested against melanoma cell lines SK23-MEL and SK29 MEL, in the same manner described supra. Cells from both of these lines were also lysed. These lines were both isolated from patients who were typed as HLA-A2, as was LB39. This suggested that the CTL clone LB39-CTL I/95 recognized an antigen presented by HLA-A2.

EXAMPLE 2

Further studies were carried out to determine if LB39-CTL I/95 also produced tumor necrosis factor ("TNF") when contacted with target cells. The method used was that described by Traversari et al., Immunogenetics 35: 145–152 (1992), the disclosure of which is incorporated by reference. Briefly, samples of the CTL line were combined with samples of a target cell of interest, in culture medium. After 24 hours, supernatant from the cultures was removed, and then tested on TNF sensitive WEHI cells. In addition to LB39-MEL and SK23-MEL, described supra, another HLA-A2 line, i.e., SK29-MEL.1, an HLA-A2 loss variant, i.e., SK29-MEL.1.22, and a non HLA-A2 line, i.e., MZ2-MEL, which is HLA-A1 positive, were tested.

Figure 2:
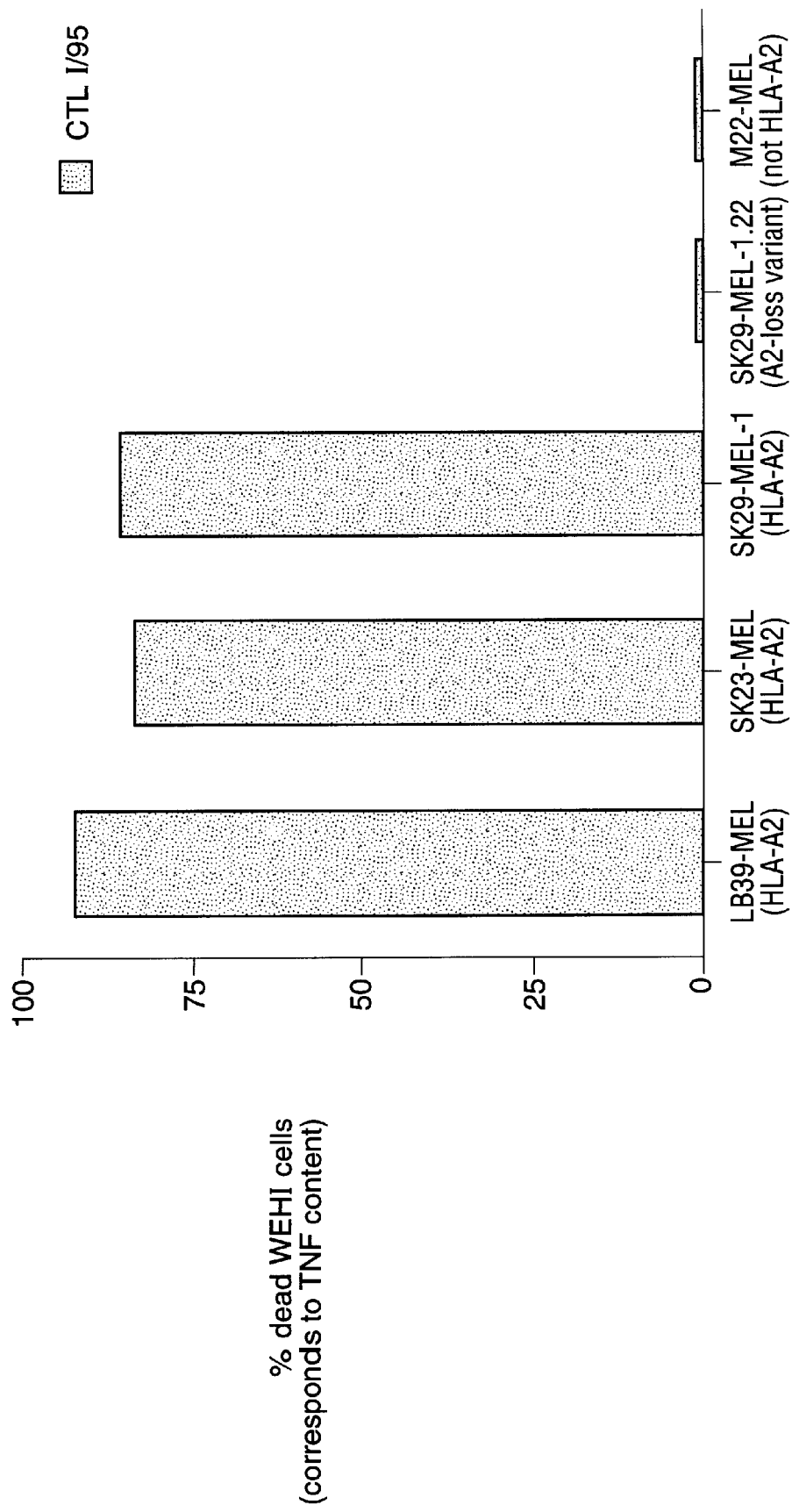
FIG. 2 sets forth results of a TNF release assay using various cell lines with CTL I/95.

The results, presented in terms of the percentage of WEHI cells which died upon exposure to the supernatant, are shown in FIG. 2. These results show that the HLA-A2 loss variant SK 29-MEL.1.22 is no longer capable of stimulating the CTL clone, thus confirming that the antigen recognized by LB39-CTL-I/95 is presented by HLA-A2.

EXAMPLE 3

The results from Example 2 indicated that SK29-MEL.1 presented the target antigen of interest. As such, it was used as a source of total mRNA to prepare a cDNA library.

Total RNA was isolated from the cell line. The mRNA was isolated using an oligo-dT binding kit, following well recognized techniques. Once the mRNA was secured, it was transcribed into cDNA, again using standard methodologies. The cDNA was then ligated to EcoRI adaptors and cloned into the EcoRI site of plasmid pcDNA-I/Amp, in accordance with manufacturer's instructions. The recombinant plasmids were then electroporated into JM101 *E. coli* (electroporation conditions: 1 pulse at 25 $\mu$farads, 2500 V).

The transfected bacteria were selected with ampicillin (50 $\mu$g/ml), and then divided into 800 pools of 100 clones each. Each pool represented about 50 different cDNAs, as analysis showed that about 50% of plasmids contained an insert. Each pool was amplified to saturation, and plasmid DNA was isolated via alkaline lysis, potassium acetate precipitation without phenol extraction, following Maniatis et al., in Molecular Cloning: A Laboratory Manual (Cold Spring Harbor, N.Y., 1982).

EXAMPLE 4

Following preparation of the library described in Example 3, the cDNA was transfected into eukaryotic cells. The transfections, described herein, were carried out in duplicate. Samples of COS-7 cells were seeded, at 15,000 cells/well into tissue culture flat bottom microwells, in Dulbecco's modified Eagles Medium ("DMEM") supplemented with 10% fetal calf serum. The cells were incubated overnight at 37° C., medium was removed and then replaced by 30 $\mu$l/well of DMEM medium containing 10% Nu serum, 400 $\mu$g/ml DEAE-dextran, 100 $\mu$M chloroquine, 100 ng of plasmid pcDNA-I/Amp-A2 and 100 ng of DNA of a pool of the cDNA library described supra. Plasmid pcDNA-I/Amp-A2 contains the HLA-A2 gene from SK29-MEL. Following four hours of incubation at 37° C., the medium was removed, and replaced by 50 μl of PBS containing 10% DMSO. This medium was removed after two minutes and replaced by 200 μl of DMEM supplemented with 10% of FCS.

Following this change in medium, COS cells were incubated for 48 hours at 37° C. Medium was then discarded, and 1000 cells of CTL I/95 were added, in 100 μl of Iscove's medium containing 10% pooled human serum, supplemented with 25 U/ml of IL-2. Supernatant was removed after 24 hours, and TNF content was determined in the assay on WEHI cells, as described by Traversari et al., supra, previously incorporated by reference.

Of the 800 pools tested, 99% stimulated TNF release, to a concentration of from 3–6 pg/ml in the supernatant. Two pools gave yields over 8 pg/ml, with a duplicate well also yielding over 8 pg/ml.

EXAMPLE 5

Figure 3A:
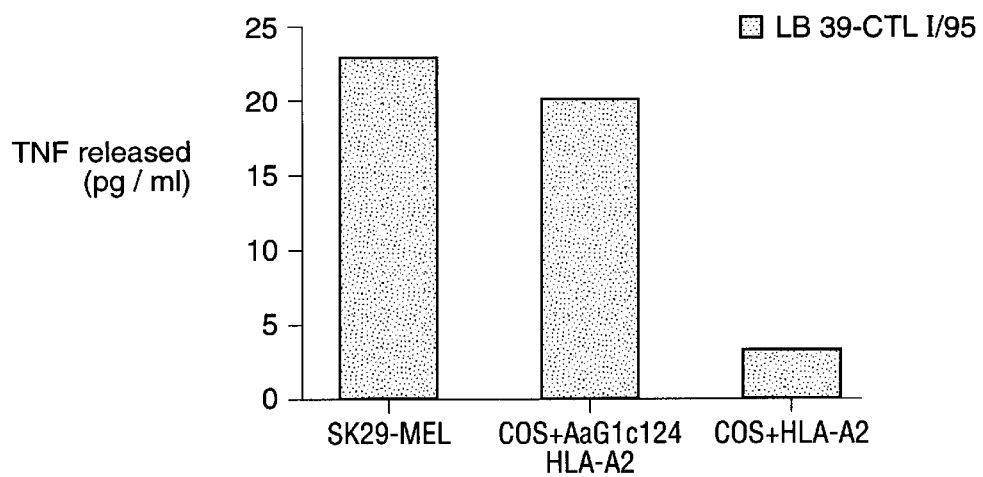
FIG. 3A shows TNF release induced by different cell lines, including transfectants, when tested with CTL clone I/95.

The two pools showing high yields of TNF in the supernatant were selected for further study. Specifically, the bacteria were cloned, and 800 bacteria were tested from each pool. Plasmid DNA was extracted therefrom, transfected into a new sample of COS cells in the same manner as described supra, and the cells were again tested for stimulation of LB39-CTL clone I/95. One positive clone was found, referred to as AaGlcl24. Convincing evidence that the transfected cells were recognized by CTLs was obtained by carrying out a comparative test of COS cells transfected with cDNA from the positive clone and the HLA-A2 gene, COS cells transfected only with HLA-A2, and cell line SK29-MEL. TNF release in CTL supernatant was measured by testing it on WEHI cells, as referred to supra. The optical density of the surviving WEHI cells was measured using MTT. FIG. 3A shows the results obtained with CTL clone I/95.

Figure 3B:
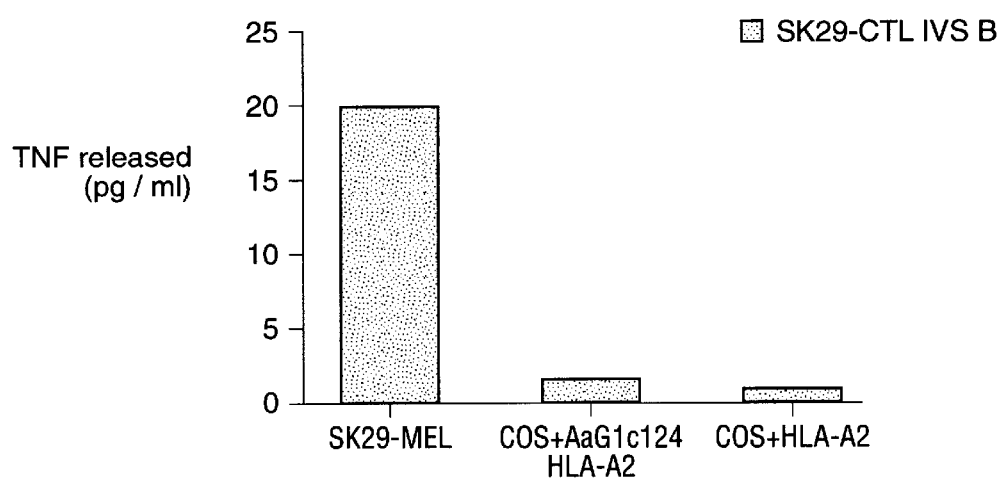
FIG. 3B presents TNF release data using CTL clone IVSB.

Further tests showed that the peptide presented by HLA-A2 in the transfected cells was different from that observed previously, i.e., a tyrosinase derived peptide. CTL clone IVSB is specific to complexes of tyrosinase derived peptide and HLA-A2. When this CTL clone was contacted to cells transfected with AaGlcl24 and HLA-A2, TNF release was minimal, as shown in FIG. 3B.

EXAMPLE 6

The cDNA from the positive clone was removed, and sequenced following art known techniques. A sequence search revealed that the plasmid insert showed no homology to known genes or proteins. SEQUENCE ID NO: 1 is a cDNA sequence representing the mRNA transcript of SEQ ID NO: 2, which is the full tumor rejection antigen precursor coding molecule, i.e., the genomic clone. The cDNA sequence sets forth a large, open reading frame at nucleotide positions 75 to 431.

The complete nucleotide sequence for SEQ ID NO: 2 has not yet been deduced. Much of it has. There is a uncoded region which follows nucleotide 9422 which is from about 4.7 kilobases to about 5.3 kilobases in length. This is SEQ ID NO: 12. As nucleotide sequence is inherent to a nucleic acid molecule, further details are not provided.

EXAMPLE 7

Figure 3C:
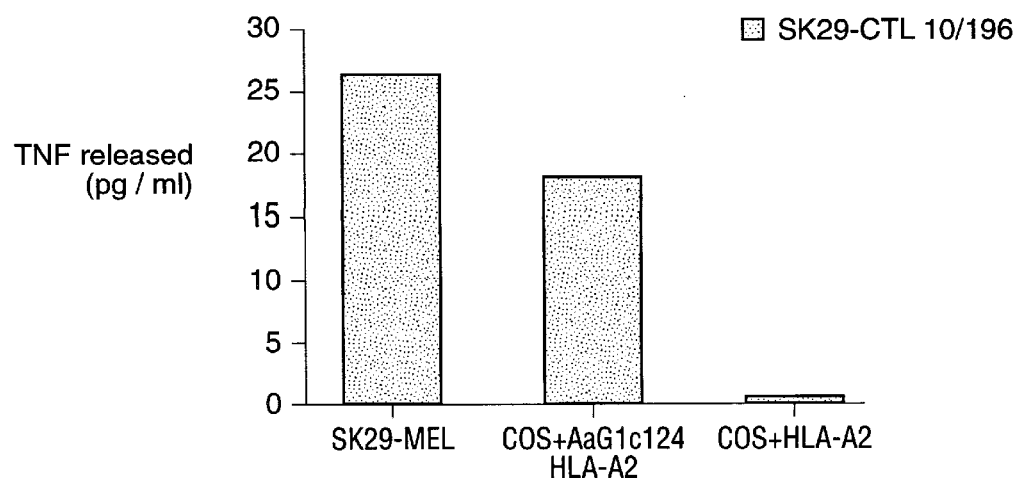
FIG. 3C shows TNF release using CTL clone 10/196.
Figure 5:
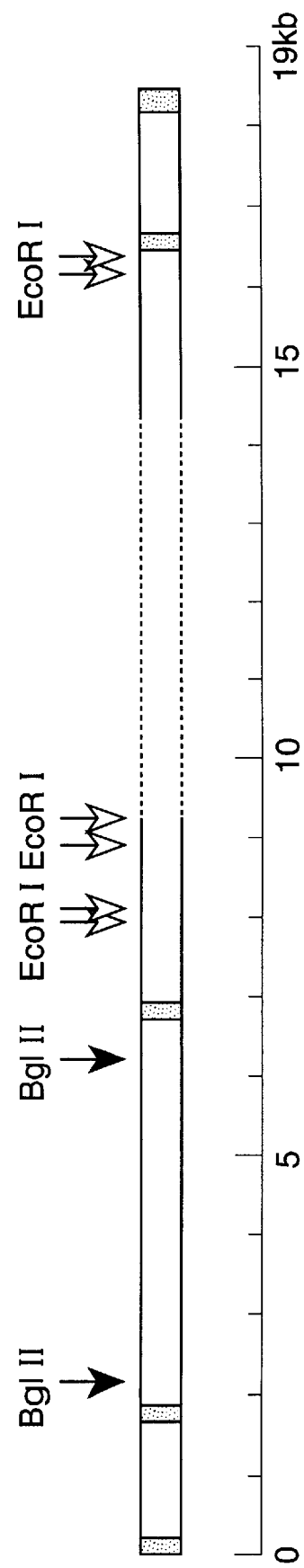
FIG. 5 sets forth, schematically, the structure of gene Melan-A, where exons are presented as black boxes, and restriction sites are depicted. Stippling represents unsequenced portions of the gene.

In the same manner that CTL clone LB39-CTL I/95 was isolated, a sample of PBMCs and a melanoma cell line developed from patient SK29(AV) were used to isolate CTL clone SK29-CTL 10/196. This new cell line was tested in the same manner as is set forth in Example 5. The results of the assays, depicted in FIG. 3C, show that the tumor rejection antigen coded for by AaGlcl24 (referred to as antigen "LB39-Aa" hereafter), is also recognized by this CTL clone. These experiments indicate that other patients can, and in fact do, generate CTLs specific for this antigen.

Oligonucleotide probes were derived from the described sequences, and were used in standard polymerase chain reaction methodologies to determine expression of the gene in normal tissues, tumors, and tumor cell lines. These results are presented in FIG. 4, and show that among normal tissues tested, only melanocytes expressed the gene. Note the expression in all tumor samples and/or melanoma cell lines tested.

EXAMPLE 8

The cDNA described supra is 675 base pairs long. It was used, as a probe, with total RNA of melanoma cell line SL20-MEL.1. A Northern blot was carried out, in accordance with Van den Eynde, et al., J. Exp. Med. 173: 1373 (1991), incorporated by reference herein, and identified a band of approximately 0.75 kilobases. Following this, the 675 base pair long sequence (SEQ ID NO: 1) was used to probe cDNA derived from SK29-MEL, using the same methodology elaborated upon, supra, for screening cDNA. A clone of 760 base pairs was identified, and SEQ ID NO: 3 sets it forth. The sequence differs from SEQ ID NO: 1 in having 83 additional base pairs at its 5'-end.

EXAMPLE 9

The gene corresponding to the cDNA described supra was then isolated. To do so, a genomic library of total human DNA (700,000 independent cosmids) was constructed in cosmid c2RB, using DNA from melanoma cell line LB33-MEL, following the methodology of DePlaen, et al., Proc. Natl. Acad. Sci. USA 85: 2274 (1988), incorporated by reference herein. DNA was isolated from 22 groups of 70,000 cosmids, and subjected to standard Southern blotting, using as probe, $^{32}p$ labelled SEQ ID NO: 1. The probe hybridized to nine groups. The group that produced the strongest hybridization band was subcloned, and then subjected to colony hybridization, again using the labelled cDNA. The cosmid which gave the strongest signal was then sequenced, using primers deduced from the cDNA sequence, viz:

OPC 69:5' GTA AGA GTG GCC GTG CCC CT 3' (SEQ ID NO: 4)
OPC 70:5' 5' CCA TCA AGG CTC TGT ATC CAT T C' (SEQ ID NO: 5)
OPC 71:5' ATA AAA GTC TTC ATG TTG GCA CTC 3' (SEQ ID NO: 6)
OPC 72:5' ACA GGT TCA CAG TTT TTC TCT TGA AG 3' (SEQ ID NO: 7)
OPC 73:5'GTA GGT CCG CTA GCA GTA C 3' (SEQ ID NO: 8)
OPC 75:5' AGA AGC AGT CTT CAT ACA CGC GG 3' (SEQ ID NO: 9)

The sequencing work revealed a first intron of 1512 base pairs, a second one of 5 kilobases, a partial sequence of the third intron, and a fourth intron of 1462 base pairs.

In further experiments, the cosmid DNA was digested with EcoRI and Bgl II, it having been determined from the sequences that these restriction sites were present in the gene. Oligonucleotides were prepared on the basis of each of the sequenced introns, labelled with $^{32}p$, and utilized in a standard Southern blotting experiment, using the digests referred to supra. This work led to hybridization of a 7 kb EcoRI fragment with $^{32}$p labelled oligonucleotides from the ends of intron 3. Estimated size of the intron was 9.5 kb, leading to a total length for Melan-A of about 18.5 kilobases. This estimation results from several datum, viz:

(i) the fact that in the Southern blotting work the oligonucleotide bound to either side of a 7 kb EcoRI fragment; and (ii) the fact that 2.5 kilobases of intron 3 of the gene had already been sequenced upstream of the EcoRI site located furthest downstream.

EXAMPLE 10

The pattern of expression of Melan-A was analyzed, using reverse transcription and polymerase chain reaction (PCR). To carry out the work, total RNA was isolated from tumor samples, following Davis, et al., (Basic Methods in Molecular Biology, 1986, New York, Elsevier, pp 310), or was secured from melanocytes.

Reverse transcription was performed on 2 ug of total RNA per sample, using an oligo (dT) primer. Samples of cDNA corresponding to 100 ng of total RNA ($10^4$ cell equivalents), was amplified for 35 cycles at 63° C. by PCR, using primers:

5'-ACTGCTCATCGGCTGTTG-3' (sense) (SEQ ID NO: 10)

5'-TCAGCCATGTCCAGGTG-3 (antisense) (SEQ ID NO: 11)

These primers are located in exons 3 and 5 of the Melan-A gene (SEQ ID NO: 2), and are used to exclude amplification of any genomic DNA contaminants. Aliquots of PCR reaction were run on 1% agarose gels, stained with ethidium bromide. To ensure that there was no degraded RNA, cDNA products were tested for the presence of human β action.

The results are presented in Table 1, which follows. Out of twenty-one melanoma cell lines, twelve were positive. With respect to normal tissue, only melanocytes were positive. Where skin biopsies were positive, it is presumed that this is because of a higher than usual proportion of melanocytes.

TABLE 1

Expression of the Melan-A gene.

|  | Proportion of positive samples |
|---|---|
| Normal tissues |  |
| Melanocytes | 2/2 |
| Skin | 2/3 |
| Liver | 0/1 |
| Kidney | 0/1 |
| Heart | 0/1 |
| Prostate | 0/1 |
| Breast | 0/4 |
| Ovary | 0/1 |
| Testis | 0/2 |
| Adrenals | 0/3 |
| Lung | 0/2 |
| Fetal brain | 0/1 |
| Cerebellum | 0/1 |
| Substantia Nigra | 0/1 |
| Tumors |  |
| Melanoma samples | 26/26 |
| Melanoma cell lines | 12/21 |
| Breast tumor samples | 0/5 |
| Sarcoma samples | 0/5 |

TABLE 1-continued

Expression of the Melan-A gene.

|  | Proportion of positive samples |
|---|---|
| Non small cell lung tumor samples | 0/5 |
| Renal carcinoma samples | 0/4 |
| Colon carcinoma samples | 0/4 |

The foregoing experiments describe isolated nucleic acid molecules coding for a tumor rejection antigen precursor, a "TRAP" molecule, in the form of genomic DNA, cDNA and mRNA. The protein molecule for which these code is processed intracellularly in a manner which leads to production of at least one tumor rejection antigen, or "TRA", which is presented by HLA-A2 molecules. While it has been observed previously that HLA-A2 molecules present peptides derived from tyrosinase, the nucleic acid molecules of the invention do not code for tyrosinase, and the TRAs are not tyrosinase derived.

The invention thus involves isolated nucleic acid molecules which code for a tumor rejection antigen precursor, or "TRAP", with the proviso that the TRAP is not tyrosinase such as, but not being limited to, SEQ ID NOS: 1, 2 and 3. The TRAP coded for is one which is processed to at least one tumor rejection antigen, or TRA, which is presented by HLA-A2 molecules on cell surfaces. The nucleic acid molecules of the invention may be, e.g., genomic DNA, ("gDNA"), complementary DNA ("cDNA"), or a form of RNA. The invention also involves isolated nucleic acid molecules which are complementary to the molecules described above. An especially preferred form of the invention are molecules which contain the sequence set forth in SEQ ID NOS: 1, 2 and 3.

Also encompassed by the invention are vectors which contain the nucleic acid molecules of the invention, operably linked to a promoter. The vectors may also include a molecule coding for HLA-A2. As these two molecules, i.e., HLA-A2 and the TRAP, are necessary to generate a cytolytic T cell response, the invention also encompasses expression systems where nucleic acid molecules coding for TRAP and for HLA-A2 are presented as separate portions in, e.g., a kit. The invention also encompasses cell lines transfected by the vectors described herein, be these prokaryotic cells, such as E. coli, or eukaryotic cells, such as Chinese hamster ovary ("CHO") or COS cells.

As indicated, the complexes of TRA and HLA-A2 provoke a cytolytic T cell response, and as such isolated complexes of the tumor rejection antigen and an HLA-A2 molecule are also encompassed by the invention, as are isolated tumor rejection antigen precursors coded for by the previously described nucleic acid sequences.

The invention as described herein has a number of uses, some of which have already been described. First, the identification of a tumor rejection antigen which is specifically presented by HLA-A2 molecules, as well as a nucleic acid molecule coding for its parallel tumor rejection antigen precursor permits the artisan to diagnose a disorder, such as melanoma, characterized by expression of the TRAP. These methods involve determining expression of the TRAP gene, and/or TRAs derived therefrom, such as TRA presented by HLA-A2. This can be accomplished by using the recited sequences, or fragments thereof, as probes, primers, and so forth. Other TRAs may also be derived from the TRAPs of the invention and presented by different HLA molecules. In the former situation, such determinations can be carried out via any standard nucleic acid determination assay, including the polymerase chain reaction, or assaying with labelled hybridization probes. In the latter situation, assaying with binding partners for complexes of TRA and HLA, such as antibodies, is especially preferred.

The isolation of the TRAP gene also makes it possible to isolate the TRAP molecule itself, especially TRAP molecules containing the amino acid sequence encoded by SEQ ID NO: 1. These isolated molecules, when presented as the TRA, or as complexes of TRA and HLA, such as HLA-A2, may be combined with materials such as adjuvants to produce vaccines useful in treating disorders characterized by expression of the TRAP molecule. In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to prove a CTL response, or be cells which express both molecules without transfection. Further, the TRAP molecule, its associated TRAs, as well as complexes of TRA and HLA, may be used to produce antibodies, using standard techniques well known to the art.

When "disorder" is used herein, it refers to any pathological condition where the tumor rejection antigen precursor is expressed. An example of such a disorder is cancer, melanoma in particular.

Therapeutic and some diagnostic approaches presented in this disclosure are premised on a response by a subject's immune system, leading to lysis of TRA presenting cells, such as HLA-A2 cells. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. COS cells, such as those used herein are widely available, as are other suitable host cells.

To detail the therapeutic methodology, referred to as adoptive transfer (Greenberg, J. Immunol. 136(5): 1917 (1986); Reddel et al., Science 257: 238 (Jul. 10, 1992); Lynch et al., Eur. J. Immunol. 21: 1403–1410 (1991); Kast et al., Cell 59: 603–614 (Nov. 17, 1989)), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the HLA/TRA complex. This can be determined very easily, as the art is very familiar with methods for identifying cells which present a particular HLA molecule, as well as how to identify cells expressing DNA containing the indicated sequences. Once isolated, such cells can be used with a sample of a subject's abnormal cells to determine lysis in vitro. If lysis is observed, then the use of specific CTLs in such a therapy may alleviate the condition associated with the abnormal cells. A less involved methodology examines the abnormal cells for HLA phenotyping, using standard assays, and determines expression via amplification using, e.g., PCR. This diagnostic approach need not be, and is not linked, to the previously stated therapeutic approach, as a diagnostic method is per se useful.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88: 110–114 (January, 1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining the tumor rejection antigen or the precursor itself with an adjuvant to facilitate incorporation into HLA-A2 presenting cells which present the HLA molecule of interest. The TRAP is processed to yield the peptide partner of the HLA molecule while the TRA is presented without the need for further processing.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated nucleic acid molecule which encodes a protein having the amino acid sequence of the protein encoded by nucleotides 75–428 of the nucleotide sequence set forth in SEQ ID NO: 1.

* * * * *

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 676 base pairs
      (B) TYPE: nucleic acid
      (C) STRANDEDNESS: single (D) TOPOLOGY: linear (xi) SEQUENCE DESCRIPTION: SEQ ID NO: 1:

| | | | | | |
|---|---|---|---|---|---|
| TCTTCATACA | CGCGGCCAGC | CAGCAGACAG | AGGACTCTCA | TTAAGGAAGG | TGTCCTGTGC | 60 |
| CCTGACCCTA | CAAGATGCCA | AGAGAAGATG | CTCACTTCAT | CTATGGTTAC | CCCAAGAAGG | 120 |
| GGCACGGCCA | CTCTTACACC | ACGGCTGAAC | AGGCCGCTGG | GATCGGCATC | CTGACAGTGA | 180 |
| TCCTGGGAGT | CTTACTGCTC | ATCGGCTGTT | GGTATTGTAG | AAGACGAAAT | GGATACAGAG | 240 |
| CCTTGATGGA | TAAAAGTCTT | CATGTTGGCA | CTCAATGTGC | CTTAACAAGA | AGATGCCCAC | 300 |
| AAGAAGGGTT | TGATCATCGG | GACAGCAAAG | TGTCTCTTCA | AGAGAAAAAC | TGTGAACCTG | 360 |
| TGGTTCCCAA | TGCTGCAGGT | GCTTATGAGA | AACTCTCTGC | AGAACAGTCA | GGACCACCTT | 420 |
| ATTCACCTTA | AGAGCCAGCG | AGACACCTGA | GACATGGCTG | AAATTATTTC | TCTCACACTT | 480 |
| TTGCTTGAAT | TTAATACAGA | CATCTAATGT | CTCCTTTGG | AATCCTGTAG | GAAAAATGCA | 540 |
| AGCCATCTCT | AATAATAAGT | CAGTGTTAAA | ATTTTAGTAG | GTCCGCTAGC | AGTACTAATC | 600 |
| ATGTGAGGAA | ATGATGAGAA | ATATTAAATT | GGGAAAACTC | CATCAATAAA | TGTTGCAAAT | 660 |
| GCATAGTAAA | AAAAAA | | | | | 676 |

(2) INFORMATION FOR SEQ ID NO: 2:

(i) SEQUENCE CHARACTERISTICS:
        (A) LENGTH: 9421 base pairs
        (B) TYPE: nucleic acid
        (C) STRANDEDNESS: double
        (D) TOPOLOGY: linear (ix) FEATURE:
        (D) OTHER INFORMATION: Following position there is an
            unsequenced portion of from 4.7 to 5.3
            kilobases (xi) SEQUENCE DESCRIPTION: SEQ ID NO: 2:

| | | | | | |
|---|---|---|---|---|---|
| CCGTCAGAAA | TCTAAACCCG | TGACTATCAT | GGGACTCAAA | ACCAGCCCAA | AAAATAAGTC | 60 |
| AAAACGATTA | AGAGCCAGAG | AAGCAGTCTT | CATACACGCG | GCCAGCCAGC | AGACAGAGGA | 120 |
| CTCTCATTAA | GGAAGGTAAG | AGCGTTGCCT | TCTCGCCATA | ATCATAGTCC | TCTTCTCCCA | 180 |
| GAATAGGATT | TGGAAATTC | TGGCTAAGTC | CTCTGCCTAC | CCTCATTGCC | CCGCTGATGT | 240 |
| GTGACATCAA | CAGAATTTCT | CCGCAACGTT | TGTCAGTCTC | CAACCTCAGA | GGGCTCACAA | 300 |
| AGCCTCCTCC | TGAATCCTCT | CTCAGTCCTC | CAACACTACC | AAGAAGAAAA | GCAATTATTC | 360 |
| AGGATGGCAT | CTTGCTGGGG | AGAAGCAGCC | TCCCTGAGGT | AGATGTGTTC | TCCTGTCACT | 420 |
| TAAAGAACCA | CTTCTCCTGG | TCTGAGTAGT | AAGAGGCGCA | TTTGCTGTTG | CTGCACCATT | 480 |
| TGCCAAGGCT | CTGAGTTTGA | GGTATGGGAT | GTATTAAAAC | AATTTAATGA | AGAATTAAGA | 540 |
| TTCCATTCTG | TCATTTTGAA | CACAGGGTTC | AGTCCTATAT | TATTCACTTG | AGAGGACTGG | 600 |
| TGAGTTTGAC | TTTCATTTCT | TTTTTACAAC | TGGGAAGGGC | AAATTACACA | TAAAATGTCC | 660 |
| CAGTGGAAAG | GGGTCATGTG | TCGAAATCCC | CACTCTTCTG | TCTCACCTCT | CCCTGTTGTT | 720 |
| TTAAACTGGG | GCTCATTAAT | ATAATTCTAT | GGGGATCACA | CCTTTGAAAT | TCATGAGGAC | 780 |
| AGTAAGAGAG | CAGAAAAATA | CACAATAATA | AGGAAAGGAG | CTTCCATTAT | TGGTTTTTAA | 840 |
| TGAGCGTACT | TGAATTACGG | CCACTGCaGT | TTATGGATAT | TTTTTGTTGT | TCATTTGTAT | 900 |
| GTGTTATAGT | TAGAAAAAAA | AAGAATCCTA | GCCAAGGGAC | TTGAACCAGA | GAGAAGCAGA | 960 |
| AATTGACTTA | AGTAGGAAGG | GAAACACATT | ATTAGATAAA | GTCAGGTCCT | GGGCTTCCTC | 1020 |
| GGCTTGTTTT | GGGTGGAGTG | CCTGGGACA | GGCTGAAGCC | CCTGTGTGGG | GTGGTTTCCT | 1080 |

```
TTGCTGAAAA GCTGGGCTGG AAGATGTTGT GCTCAGTGCT CAACCTCATG CACCCTCGCG    1140

AGGCACAGGC AACGGGTGCT CTGGGAAACA CACGTTATGT ATCATAGCCT CTGTTTGTCT    1200

GTGGGATTGA TATCCAATAA TAACTTTGGA GAAAAATAAC TCCTCTTATT TTGTTAGCCA    1260

CAGCCCTGGG CCAGGGAAGG TGGAGAATCA GTGAAAATGC ATTTTGTTTG TTTCTCTAGA    1320

AGTTTATGGT GCAGAGTCAA ATTGAAGGCA AATGAGGAAT ATTTTTTCAT TAAATAATAA    1380

CTCAACTTGC AAGTCTTTTT TGCTTTTGTT TGTAGTTTCT TCTTTGAACT TAATTTTCAG    1440

TTAGTAGGAG GGGTTAGAAA CCTGAGCTAT TGCTAAAGCC CTTGATATGA ATGAAAGAAG    1500

CAGGTGCAAA TCCCCTCACA GAGAGAAACC AAAGGGTCCT GGCTATGGAT ATTGGTCACC    1560

TAGTCAGGAT GCTGTTGTGG GTCTTTATGA GATGATGAAT AGGGTGGCTT TGGATGCATT    1620

AATGATATTT ACATGCTCCT TCTGTTAGTG TCCTGTGCCC TGACCCTACA AGATGCCAAG    1680

AGAAGATGCT CACTTCATCT ATGGTTACCC CAAGAAGGGG CACGGCCACT CTTACACCAC    1740

GGCTGAAGAG TAAGTTCAAA ACCAGACCCA GCAGGGCTTC CAGTTTGCCG TTTGCTGACA    1800

CAGCCTGCTG ACTTCCACCA GTACATGCCT GCTCGTAAAT CTCCCTAGTG TTTATCTCCC    1860

CAGACAGTAA CATCCCTGGC AACAAGGGGA GGAGATTCTG TGCTTCTATA AGGGGCTCAG    1920

TCAAGCTTCT CTGAGGCCAA ACAGGCAGGA AGATGGGAAT GGTATAAGGT TGGATCTTGC    1980

CATTTTTGGG TGCACTTTTG ACTATTGGGT CTTATCTGTA GGTTCCCAAG TGGAAAAACA    2040

TCTGTTCAGG ATCACAATGC CTCTCTCCTC AATCCTTGTT CTGTCTCCTC CACTCAAATT    2100

CCTGAAGGTG GTTTGCAGAC AGAATAAAAG TGAGTTGCCA AGGAGCCAGT AAGGATGACG    2160

GGCAGGTGTG TGTGACTCAG CCCACAGCCA GACTCGAGAG GAAGATGGAG GTCACAGCCT    2220

TTGCAGTATA ACTTTATCCT AAGGAAAGAC ATTGGGTTTT ATGAGTGAAT TAAAAATAAG    2280

TATTTATATG ATTAAGCATT TCTAAATGCT AAGCATTGTA TACTGGCGTG AGACACTGTT    2340

TTTATCTTTG AAAAAACTCA CAACTTAGTG GGAGAGTTAG GCATGAGATT AATTTCAGCA    2400

AATGTAAGTG CGGTAATGAA AACCCAGAGG CTGCAGGGAC ATACTCTGTA TGTGCTGGGA    2460

GTGGGAAAGG GACATACTCT GTACGTGCTG GGTGGCAGGG GCAGGGGAGG CCCCACCCTC    2520

TGCGTGGGAC TGTAACAGGA CAACACCCTC TTATGTGGTC TGTCCAGAAC TCCCTGTGAA    2580

CCTGCTCTTT CTTTGGAAAG AGCTGTTGAA CAATCTTTGT TAACAGTCAA CCGCAGGACC    2640

AGCAAGATGT AAAGCCCAAC AAAGGCACTG AGGAAGAGTT CAGGNAGACA GCATTTCCTC    2700

AGAAGACCCT GGTATAGGAT CCTCTAATAT CCCTGGCCAA TTGGAGATGA GGGCGGCGGT    2760

ATCCTCTCAG AAAATGTCCT GACAGCAAAA ACATACTCTT TGAGGGAGGG GAGCCCATTG    2820

CCCGTGCTAT TAGTTAGGGT ATCGTTTCAG CTTGTGTATA ATCACTCAAC AGACTCTTTA    2880

AAATATACTT TTATGTCTCG TGTAAAAATT CAAGAGTAAA GAGTTCAAGG CCTGTTCGTT    2940

TTCTTCTTGC TGGTTACTCC CTTGGGATCG TCACTTTTGT CCCCATGGCT GAAGATGTTG    3000

TGCCATCACC TCCACATCTT GCCAACAGAA AGCAGGAGGT GAAGGAGAGG CTAGGACCAT    3060

TCCTTTCAAG GGGCACACGT CACTTCTGCT TATTGCTCCA CCCCCGCCCC CCGCCCCGTG    3120

GCACCCACCC TGGTGGTATC ATTCTTGCTG TGTTGTAAAT GAAGAAAGGT TTAGAGAAAT    3180

TAGGAAATGT GTGGCCAGAC ATGGTGGCGC TGGGATTTAA ATCCAGGTCT GTTTGCCTCC    3240

AGAGTCCATG CTCTTAAGTG TTATGCTGCA GGCCAGCAGA GGCAAATATT TGCACAATCC    3300

CATCCGACGA GAGGCTAGGG CAGAGGTCAG TATCTCTCAG TGTGAAGCTG GAGGCTGATG    3360

CTAGTCAGCT CAGTAGGCCG AAAGTGGAGT TGTCCTTTGC CATGTAGGGC CATCATGCCC    3420
```

-continued

```
AGCTGGGGAA CCTCATAGCC AGGTGTACCC ACAACCTGAA CAAGGTAACT TTCAGGGTCT    3480

AGTCAGGAAG AAACCAACTA GATGGTTCAA CATAGAGACT TTAATATAAG AAGCTGGTTA    3540

AACAGGCATG GGACTGAGAC TGAGGAGGCA AAGAAGGCAT CGGGGCAACC AAGGCTGTAC    3600

CCACAGAATG CTGCTTCTAC CCCCGTGTCT GGGGTAACAA ACGGAAGGGT GAGGCCATCA    3660

GGACCTAGAG TTGGGAGGAG GGACGCCACA GAAATGGGAC CCAGATCTCT AAGGAGAGAT    3720

TTTTGTTTGG CTGGTTCTGG TGTCTCAAGA GCTTAGAAGT GAGGGGCATG AATCAAATAC    3780

TCAGGCCTCT GAGGTCAGCC AGTGCTCTGC TGGGGAGGGG CATAATGAAG CTGGCTCTGA    3840

CAATGCCGGA AAACGAGCTG GTGCTTGGCA TATACAGACA ATGTGAGCAT TGCTGGGGTG    3900

ATCCTGACAG GAGCCAGAAG CACACTGAAA GGAGCTGCTC CTTCTTGATG CCCCAGGTTT    3960

GTAGGCACCC TCTAGAGTAC TCTAATGGGA GCCAGTGGGC AAAGGAGAAG TGGCATTTGC    4020

AGAGTCCAGT CCCAGCATCA CAGAGCAGAG CATAGAAAGG TAGGTTTGGA GAAGAGGGAC    4080

AATGGCTTAA TAAAGGGCAA AGGGGGTTAT GACCACTATC ATGTGAAGGA ACCCCTTGAC    4140

TGAAGGCACA AGCTTTCTGT GTCTTGCAAC CTGAATGACG TGCATAAGCA GGGTCAGGTG    4200

GGTTATCTGA CATTTTCCTT GAGAACAAGA GGGAGCCTCT GGATTCCAGC ACAAAAGAAA    4260

AATACCCACT CAACCCGTAT GCGTGGGAGC TATCCTTTAA AGAGAAAGTA ATTCCTTTTG    4320

ACATTTGCT GTCTGTAGAA GGGTCAGATG GCCAAAGCTT CCAGCACAAT GAAACACTTA    4380

ACTTCAGTCT GTGAGTGTAG GAACCCCTGA ATACATGGAA CATCATCATC TTGTGCAGGT    4440

ACTGAAGGAG ATCGGTCCAG AAAATAAGTA ACTGCACATG GCCACCAATG TCAAAAGTCA    4500

TTCCTCTCAT GAAAAGTCCC TGCCCCCATT GCTGTTTGTT TAAATAGGTG GGATGGAGGT    4560

AGGGGAATGG GGCCATCTTC TTTTTTTTTT TTTAATTTTT TTGCATAAAA TCCAGATCCT    4620

GCACAATGGG GCAATCTTCA TTAAAACAAT GCATCCCTAA GATCTGAGAA TATTTATCCT    4680

TCTCACAATT GTGCCAGCAG GTGGAATGAA GAAGAATGAT GCAAAATAAG TTCCCACATC    4740

CAGCCAAGAA GGACTACATA CCTGCTTTGG GTATTATGTA TCCCTTTGAA ACCTCAGTGG    4800

AGAGCAGTTC TCACAGTTGG GTGGACACAA GTCATCCATG GAACTTGTTA AAATGCAGAT    4860

TTCTAGGTGC TGCCACCTAA GAGGCTGATT GGGTAGGCCA GGGGTGGAGT CCTATGATCT    4920

GCACCTTAAC GTGCATCTCA GGTGATTCTG CTGCAGGTGG TATTTGGAAG ACACTCTGAG    4980

GCGCCCTGCC AAGCTGGGCA GTGGGTTCTT CCAATGTGTC AGGCATACCC TGGTGCTTTT    5040

CGCTCTCAGT CACTTGGGCA TGTTGTGAGT ACCACGTGAC CATGCATAAA GTGCTGTAAC    5100

AGAGCTCTGT CTGTGTCAAG ATATTCAAGT GGACGCCACA GGGTAAAATG AGAGCACAGG    5160

CATGTTGGGA GTTGAATCAG CTGCCTTCAG TCACGAGAAC ACACTGAACA CTCCTTGTGA    5220

CAGCTTCAGT TCAGGAAAGA GTGACTCTGC AGGAAAAGCA CTGGCCTGGG AGACCTGGAT    5280

CTGGCCCAAA TTCTGGTGCT CACTTGCTTG GTCTCCCGTT CCAGTTGCTG TGAATGTTGG    5340

TTCTGCCACT TGCTGGTTGT GCAGCCCTGG GCACTTGACC AGCATAATGT CAGCTGTAAA    5400

ATGAACATCA TTCCTAACTC CGAGGACTGT GGTTAGGATG AAATAAAAGC ATATATGTGG    5460

GGGTGCCTAG CCCAGTGCCT GGCACAAATT GGTGCTCAAT GAATGGTAGT CACTATGGTT    5520

ATGGTAATGT TGATGAATCT TCATAGGTCT CAGCTTCCTG ATCTATAAAG CGGGTGGACT    5580

GACCTACATA AGTCAGAGTT CCATCTAGC ACTGTCATCC CATGGTTCGC TCTATCCTGT    5640

TTGGAGACGG ACAGGATAAG CTTGATGTCT CCTCAGCCTT GAGACAGAAG TTGTCCAGTA    5700

GATGGTACTG AGCAAAAGTC TCTCCAGCAG AAGCCTTAGT TAAACCTTGC TTCTCCTGTA    5760

GCTGCTCAGT CTCTTGTAAG TCACTCAGCT CTGCAGAAAC TTTCTTAGCG AGTTGACAAC    5820
```

-continued

```
CACAGATAAC AGAGTCAGTT CTGTCGATTT TGATCATGCT GTGATCAGGC AGATGTTAGC    5880

TAATTGATGA TGCTTGCCCG GAGTGAACAG CTCCAGGCCC TGTTTCCAGG GTCTTTGTGG    5940

TAACTTTGTG GTAACTGTAA TGCTTCCCAG GGGTCACTGA ACACAGGGCC CAAGAGGCTG    6000

GTGTAGACCC CCAGATTGGC ACCCTGCTGC TTAGACAAGA TCCTTCTCAA TAAGTAATGC    6060

CATAGCTTTG CTGTAGGTTC AGCCCAGACA CTTCTCCCTA GGGCTGCAAG GAGCAAAGCG    6120

GGGAGTTTAG GGAAGGGAGG GCACGAACAT AATTGAGACG GATTCAGGTT CAAATCCAGC    6180

CTCTGTTTTG TGCTAGCTCT GTATGATCAC CAGCGAGTCA TGTATCCTCT GCCTTTTATT    6240

TCCTCTTCTG TGAAAATAGG GGATGATAAA TTGTGTCTAC CCTCCAGTGT TGATGTGAGA    6300

ATTGAATAAG CTAATGAATG TTTAGCACAG CACCTGGCTT TTAGTAGATG AGTCAGTGTT    6360

AATTTCTATT TTCTCTTTGT GGGCTGAGTT GGAGAAAATG TTTTAAAACA GCCTGATGAG    6420

AAGAAAAGAT AATTTAGCCC CAATAAATAC ATTGTCCACA TAAAGACAGT TACTATGGCA    6480

CTTCTCATAC CTGGAACTTG GGTGCCTGGG CCATGCAATT AGCAGAGTTC CTGTGGGCAC    6540

ACACTTGAGA GGCTCCTAAA GACCTGGGTT AGATCCAGGT GCTGGAGGCC TGGTGGGGTG    6600

CCAGTGTGGG AGGTGGGAAA CTACTTGGAC ACTGGGAGAT GCTGCTCTGG GTCGTCAAAG    6660

TCCATATGAA GAGGAAGACT GATTTATGCT TCATCATAAT GTAGAACAAT GTTTCAATGA    6720

CAAAGTGGAT TTGTCTATCT CTTGGGCCAG GCCGCTGGGA TCGGCATCCT GACAGTGATC    6780

CTGGGAGTCT TACTGCTCAT CGGCTGTTGG TATTGTAGAA GACGAAATGG ATACAGAGCC    6840

TTGATGGTTG GTAAAGTTCC CACTGCTGAA ATCCCTCCAA GTCCAGGGCC CTCTTTCCAG    6900

TTCTTTCCTC TGAATCTCTG GAGAGTCAGA TAATTGCCTC ATTATAACCT TCAGCTCTGA    6960

TTCCGGCTTC TGATGCCTCT TTTGCTACAT TGTACTTTGG CAACTCTACC TTTGCCTCTG    7020

CTCAGGCATG AACCTCAACC AGGAACTTGC CCTGTGTCTT AGTCTGTGAT TATAACATAA    7080

TACGAGAGAC TGTAATTTAT AAATAAATGA AATTCATTTG GTTTACAGTT GGGAGGCTGG    7140

GAACTCCAAG ATCTAGGGGC CACACCTGGT GAGGACTTCT TGCTGTGTCA TATCATAGTG    7200

GAAGGCATCA CATGGGCAAG GGAGTGAGAG AGCAAGAGGG AGCTGAACTC ATTTTTTTTT    7260

TTTCTTGAAA CAGGAAATCC TGGGATGGAG CGCAGTGGTG ATCATGAGTC ACTGTAGCCT    7320

TGACCTCCTG GGCTCAAGCC ATCCTCCTGT CTCAGCCTCC AGAGTAGCTG GGACCACAGG    7380

CACGTGCCAC CACACCGGCT AATTAAAAAA AAACTTTTTT TTGTAGAGAC GAGGTCCCAC    7440

TATGTTGCCC TAGGCTGGTC TCAAACTCCT GGGCTAAAGT GATCCTGCCT CGGCCTCCCA    7500

AAGTGTTGGG ACTACAAGTG TGAAACACTC CACATATGGC CCAAACTCAC TTTTATAACC    7560

AACCTACTTT TGCAATAACA AACACACTCC TGCAATAACA CAATTAATCC ATTCGATGAG    7620

GACAGAGCCC TTGTAACTTA ATCGACCTCT TAAAAGTCCT GCCTGTTACC ATTGTTGCAT    7680

TGGGGATTAG GTTTCCAATA CACGAATTTT GGGGACACA  TTCAAACTAT AGCACCTGTC    7740

TCTTTGGTTC TACTCATAGC AGACTTGGGT ACCTGGATGT TGTGTGTAGC TAAGCACTGA    7800

CGGTTTATAG GGCACAGGGG AAGGGGTTTG AGGTTCCCTT ATAGCAAACA GGAGTATATT    7860

AGACACCTCA GGTTTTACCA CTTCTGGGAA TTCTTGCTGG TTCTGTTACT CCACTTTGTG    7920

ACCTGCTCTT CCTACTTTTC TTCTTCACCC CTTTCCTCAC TGGTTACCTG TGAATTCCAA    7980

GTTCTTCTGA CTCTACACTA AGCATCCCAG GATATCATCA GTGCGATGAG GAAACCATCC    8040

TTCCTGCATC AGCACAAAGG GTCACTTGTG TGTTTTTTAA CAGGCTGCAT CCTTCTTAGA    8100

TGGCCAAAGG TTTTAATAGT ATTTTTTTCT TCTTTACCCA AATATGCAGG AAGCTAACAC    8160
```

```
AATTACACAA TCCAATCTTC TGGTACCAGT ATCCTCCATG AATGGGAAAC ATCAACTGAG    8220

TTTATAAGCT ATAAAAATTA CAGGTTTCAG CAATCTTGCT TAAAGCCAGG TAGCACTTCA    8280

GCACTTCAGC ACCCGAAGCA TTCTCCATAG ATCTCGCTGT CTCTCTTTCT TGTTATTACA    8340

GATCTGAAAG CTTTTCAGGT TGATGCATAA TGGAAAAAAA GTATCTTTCC AAAAGATGTT    8400

GGAAAGTCCC ATTCTCATTC AGCAAGCACT TCATTTAGAG GAAAAGGTCC TGTGAAAGAG    8460

AGGAGGGTTG GTGTGGGGTG GGGATTGAAG CTTGGCAAGC TGATAAGGAG AAGGTGAGAG    8520

ATACAACTCT GGATTCTTTC CCTCTTTGCC AAGAAACTTG GGCAGTCTCA TGTCTCATGT    8580

CTCCTGTTCC CCAATGTCTT TCCAGAGCAT AAATACAAAT ACAAACCATC AAAGGCAAGT    8640

CAAGTCTGGG GGCTGACACA CCCACCGAGC ATAGCCCTCT AGTGTGCTGA CATCTAGTGG    8700

GAAGGAGGAG GAGTTGATGA ATCTGAACAA GACTCCAATA TTGGAGGAAA TACTTGAGGA    8760

AAGCCTTGGG TTAGAAAGTT AGGGATAGAA TTCCTGCTCA TACGGCTGTC CACAACAGGT    8820

TAGTAGGGGA GGACTTTAAT CTCTGCCATA GAACTCCATT TGTAACTCTA GCATGGGGTT    8880

ATGACATTGC CTTGTAATTG GCTATTTACT TTTTGCCTCT TCGACCCCTC CGCTTTCCCC    8940

TATGTATGAA CCACAACAGA GAATATTTCT AACTCATCTT CATATCTCCA GTGCCTAGCA    9000

CAGTGCCTGG TACATGGTAG TCACTCAATT GTGTTGCATT AGGACTTGGT CCCATTGTCT    9060

GCCATTGAGT TGCTTGGAGA CTAGAATTCA ACTTCTCCAA GATTCACTAG CTCTATTTTA    9120

CACCCAGACA TGTTGGAAAT CTGTGATGTA ACACAATGTA TATCCATTTT TATTTAATAC    9180

ATATTTTCTT CTATATTTTG ATTTCATTAT ATATTTGTAT ATCAAAAACA AAATGTTTAG    9240

TCTTTCAAGA AGTAAAGCTA TACAAACTCA ATATGTTGGT ACTCATTTCC TAACTATAAT    9300

TATTAGTTTG ATCCTATTGA ACACAAATGC AGTAATTTTT CTTTTCTGCT TCAATGCTCT    9360

CATCTTAAAT TCATTTAATT GAAAAATAAC AGAGAGTCTT AATGTCATGT GCTCAGACAC    9420

T                                                                   9421

(2) INFORMATION FOR SEQ ID NO: 3:

(i) SEQUENCE CHARACTERISTICS:
        (A) LENGTH: 760 base pairs
        (B) TYPE:  nucleic acid
        (C) STRANDEDNESS: single
        (D) TOPOLOGY:  linear (xi) SEQUENCE DESCRIPTION:  SEQ ID NO: 3:

CCGTCAGAAA TCTAAACCCG TGACTATCAT GGGACTCAAA ACCAGCCCAA AAATAAGTC      60

AAAACGATTA AGAGCCAGAG AAGCAGTCTT CATACACGCG GCCAGCCAGC AGACAGAGGA    120

CTCTCATTAA GGAAGGTGTC CTGTGCCCTG ACCCTACAAG ATGCCAAGAG AAGATGCTCA    180

CTTCATCTAT GGTTACCCCA AGAAGGGGCA CGGCCACTCT TACACCACGG CTGAACAGGC    240

CGCTGGGATC GGCATCCTGA CAGTGATCCT GGGAGTCTTA CTGCTCATCG GCTGTTGGTA    300

TTGTAGAAGA CGAAATGGAT ACAGAGCCTT GATGGATAAA AGTCTTCATG TTGGCACTCA    360

ATGTGCCTTA ACAAGAAGAT GCCCACAAGA AGGGTTTGAT CATCGGGACA GCAAAGTGTC    420

TCTTCAAGAG AAAAACTGTG AACCTGTGGT TCCCAATGCT GCAGGTGCTT ATGAGAAACT    480

CTCTGCAGAA CAGTCAGGAC CACCTTATTC ACCTTAAGAG CCAGCGAGAC ACCTGAGACA    540

TGCTGAAATT ATTTCTCTCA CACTTTTGCT TGAATTTAAT ACAGACATCT AATGTTCTCC    600

TTTGGAATGG TGTAGGAAAA ATGCAAGCCA TCTCTAATAA TAAGTCAGTG TTAAAATTTT    660

AGTAGGTCCG CTAGCAGTAC TAATCATGTG AGGAAATGAT GAGAAATATT AAATTGGGAA    720
```

```
AACTCCATCA ATAAATGTTG CAATGCATGA TAAAAAAAAA                                    760
```

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 4:
```
        GTAAGAGTGG CCGTGCCCCT                                                   20
```

(2) INFORMATION FOR SEQ ID NO: 5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 5:

```
CCATCAAGGC TCTGTATCCA TTC                                                       23
```

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 6:

```
ATAAAAGTCT TCATGTTGGC ACTC                                                      24
```

(2) INFORMATION FOR SEQ ID NO: 7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 7:

```
ACAGGTTCAC AGTTTTTCTC TTGAAG                                                    26
```

(2) INFORMATION FOR SEQ ID NO: 8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 8:

```
GTAGGTCCGC TAGCAGTAC                                                            19
```

(2) INFORMATION FOR SEQ ID NO: 9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 9:

```
AGAAGCAGTC TTCATACACG CGG                                                       23
```

(2) INFORMATION FOR SEQ ID NO: 10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 10:

```
ACTGCTCATC GGCTGTTG                                                   18
```

(2) INFORMATION FOR SEQ ID NO: 11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 11:

```
TCAGCCATGT CCAGGTG                                                    17
```

(2) INFORMATION FOR SEQ ID NO: 12:

(i) SEQUENCE CHARACTERISTICS:
        (A) LENGTH: 4129 base pairs
        (B) TYPE: nucleic acid
        (C) STRANDEDNESS: double
        (D) TOPOLOGY: linear (ix) FEATURE:
        (D) OTHER INFORMATION: The sequence is preceded by an
            unsequenced portion of from 4.7 to 5.3
            kilobases (xi) SEQUENCE DESCRIPTION: SEQ ID NO: 12:

```
GAGTGCAGTG GTATGATCTG GGCTCACTGC AAGCTCTGCC TCCTGGGTTC ATGCCATTCT      60

CCTGACTCAG CCTCCCAAGT AGCTGGGACT ACAGGTGCCC GCTACCATGC CTGGCTAATT     120

TTTTGTATTT ATAGTAGAGA TGTCATTTCA CTGTGTTAGC CAGGATGGTC TCAATCTCCT     180

GACCTCGTGA TCCACACGCC TTGACCTCCC AAAGTGCTGC GATTACAGGT GTGAGCCACC     240

GTGCCCGGCC TTATACTTCT TTTTTACTTT TTTTCAGTGG TTTCCCTAGA GTTTGCAACA     300

TACATTTACA ACTAATTCAA ATCCACTTTC AAATAACACT ATACCATTTC ATAGGCATTA     360

TGAGTATCTT AAAATAATCC TAATTCCTTC CTCCTGTAAA CTAAAAACAA AATCCTAAAT     420

CCTCCAAACA ACTGAATGGA CCCCCTCTTC ACCAAGGGGA CCCCAGGGAA ACCTGAAAAA     480

CTGAGTGTTG GCCATGACGG GAAGGGAGGT GAGAGATGCT CATTATACTC CCTCCCTTTT     540

AGAGTTTTAG GTACAACTGA CCAGCATTAA TTTTAAAATA GAGATTACAG GACTGACAGA     600

ATGAACTCTT TGTGGCAATA TCAAATTAGG AACAAGACAA TGCAAGGAAA GGGTTAAATC     660

ATGCCCTTCA AACCATAAAA AAATTTTTTT TTAATTAACC CCATATAATG TGGTATACTT     720

TCCAAACTGA CTCTGGTATA GCATCACATG ACAGATTGCA GACTCCCTTA CCTTAAGCAT     780

TCCTTTATAC TGACTTCAAG TCTTAAGACA GAGCTGAACT CTTTCAACCA GCTGCTAACT     840

AAAGAATACC TAAAACCCAC CTGTGACTTG TAAGTCTCTG CTTTGCCATG TCCTGCCTTT     900

TCAGGCTGAC CCAATGTATA CCTTCCGTGT ATTGATTTAT GATTTTTACC TACAATTCCT     960

GTCTTCCTGA AACATATAAA ACCAAATCAT AACCCAACCA CCTCAGGCAC ACTTTCTCAG    1020

GACCTCTTGA GACTATTCTC CCGGCCATGG TCATTCATAT CGGCACAGAA TGAAACCTCT    1080

TTAAAATATT TTGCAGTTTT TTTCTTTCTG TTAACATTCC TTTCCCTTGT ATCATTGCTG    1140
```

```
TTATTAATTT CAAGTATATA TAAGCATACC TAATTAAATA CATTGTTGCT ATTATTCATT    1200

TTTGAACAAA CTATTATCTG TTAAATCAAC TAAGAATAAG ACAAATATGT TGGGTGCAGT    1260

GGTGCATGCC TATAGTCTCA GCTACTCAGA GGCTGAGGCA GGAGGATTGC TTGAGCTCAG    1320

GAGTTTAAGA CCAGCCTAGG CAACTTAGCA AGATCATGTC TCTTAAAAAA AAAAAAAGAA    1380

AGAAAGAAAA ACAAAGTTTT AGGAGGCTGA GGCAGGAGTA TCACTTGAAC CCAGGACGCA    1440

GAGGTTGCAG TGAGCCGAGA TCGTGCCATT ATACTCCAGC CTGGGCAACA GAGTGAGACT    1500

CTGTCTCAAA AAAAAAAAG AAAAGAAAAG AAAAGAAAAA AAAGTTTTT ATTTTACCTT      1560

CACTTATTCC TTCTTGGATG TTCTTCCTTT ATGTAGGTAC AAGGTTCTGA CCTATGTTAT    1620

TTTCTTTTTC TCTAAAGAAC TTCAAAAGTT TCCTGCAAGG CAGGTCTACT GGCAATGAAT    1680

TCCCTCAATT TTTGCTTGAC AAAGTCTTTA TTTCTGCTTC ACTATTGATG GATAATTTCA    1740

CAAGAGTGTT CCTTTTGTAG ATTCACTCTT CTTATCCTTC CCTTCAGAAA TATTCTTTGA    1800

CCAACTATTG GGTCCCAGGT ACTGCACTAG AGCTTTACTT CTAGTTAATT CCCACAGCAA    1860

TTCTGAGAGG TAGGTAGGTA TTATATTCCT AGATGCAAAC TCAGAATTCA GAAGGTAAAG    1920

TGATGAGACT GAAGGCACAC AGCAAGTAAG TGGCAGAACC TAGATTAAAA CTCATTCTTA    1980

AAACTTTGGC TTCCTTCTCT TTTCTTTAAT GGATTCAGTT ACTTCTTCTC ACCCACTCAC    2040

CTTTATCAAT TTACATTTCA GATAAAAGTC TTCATGTTGG CANCTCAATG TGCCTTAACA    2100

AGAAGATGCC CACAAGAAGG GTTTGATCAT CGGGACAGCA AAGTGTCTCT TCAAGAGAAA    2160

AACTGTGAAC CTGTGGTAGG TTAAGATCCT TCATAAGGGT ATTTTCATGA ATGGCTGTTT    2220

TTAACTCAAG TGAATACAAT TATTTCCATT TAAAAAGCAA GGACAATGTG AATGTACTCA    2280

TTGCCACTGA ACTATATACA CCTAAAAATG GTTAAAATGG CAACTTTTAT GTGTATTTTA    2340

TGAGAATAAA AAATAAATAA TAATAAAAAA CAAGGGAAGT ACAGATATTT TCTTAATTGT    2400

GTTGTCACAT ACCCAGTGTT TCCAGGGTCA ATAATGAGAG CCCTACATGT AAGATTCAAA    2460

GGAAGAATTT AGTCCTGGAT ACAATATTCT TTTATGTTTT TAGTTATATT TGCCTTTTTA    2520

ATGGATGCAG ATATATACAG AGGGAAGGGA TAAAGTACCT ATTATTTATT GTATAGAGCT    2580

GTGCTGTCTG ATGGCTTAGC CACTAGTCAC ATGGTGCTAT TGAACACTTA AAACACAGGA    2640

GTTTGAAATA AGCATGTATT ATAATACATA TCATATTTCA AAAATATTAG TATGTAGAAA    2700

AGAAGATAAA TGGTTCATTA ATGATTTTTA TATTGATTCA CCTTGAAATA AATATTCTGA    2760

AAATATTAGG TTAAACAAAA TATTTTAAGA TTAATTTTAC ATGTTTCTTC TTTTAAATGT    2820

AGCTACTAGA AATTTTAAAA TTACATATGG CTGGGCATGG TGGCTCACAC CTGTAATCCC    2880

AGCACTTCGG GAGGCCGAGG TGGGTGGATC ACCTGATCTC AGGAGCTCGA GACCAGCCTG    2940

GCAAACATGG TGAAATCCTA TCTTTACTAA AAATACAAAA ATTAGCCAAG CGTGGTGGTG    3000

CATGCCTGTA ATCCCAGCTA CTTGGGACGC TGAGGCAGGA GAATCACTTG AACCCGGGAG    3060

GTGGAGGTTG CAGTGAGCCG AGATAGTGCC ACTGCACTCC AGCCTGGGAG ACAAGAGCAA    3120

AACTCCATCT CAAAAATAAA TAAATAAAAT AAAATTACAT AAGTGGCTTG TACCATATTT    3180

CTATTGGACA GCACTAGTAC ATATACAACA CAGCATAATG GTTGAGAGCA CTGACTCTGG    3240

AGCCAAATTA CTGTGTTTGA TTCTTAGCTC CACAACTTAC TAGTTGTGTG ACCATGGGCA    3300

AGCGAGTTAA CCTCTCTGTG CCCCAGTTTC CCATTCTGTA ACATGAAAAT AATAAAAACA    3360

CTCCCCAGAA TTGTTGTGAG CATTAAATGA AGCCCTGACA CATTTGTTCT GGATACAATA    3420

TCCTCTTGTT TTATATTTGG TAGTATCAAT GTGCCTTTAG ACACAATTAC AACGATCTCT    3480

GTGGTAAAGA TGCAATGTAT ATGGTGTCTA TAAATAGCAT TCAATGATTC GTTAGTTAGG    3540
```

```
GCTTGAGACT TTTACTGTCA TGGAAAATCT AGGTATAGCT AAGCTTTTGA GATTTTGGGA      3600

ACTCCTTAAC CCTATTTTTC TCTACTCTTG CCCCCAACAA TCAGCCTATA TACTTGTGAA      3660

ATTTAACAAT TACTTCACTG GGCAGAAATT ATATGGGAAC ACTTAGAAAT TTCAGTCCAC      3720

AGGGAAAGTA TAAATATGTT AACTATTTTA ACTTAATCCC TTCCTAGAAA CACATACACT      3780

GTTGCCAAGC CCATATTCTC CCTTTCTTGT TCTCACAGTT CCCAATGCTC CACCTGCTTA      3840

TGAGAAACTC TCTGCAGAAC AGTCACCACC ACCTTATTCA CCTTAAGAGC CAGCGAGACA      3900

CCTGAGACAT GCTGAAATTA TTTCTCTCAC ACTTTTGCTT GAATTTAATA CAGACATCTA      3960

ATGTTCTCCT TTGGAATGGT GTAGGAAAAA TGCAAGCCAT CTCTAATAAT AAGTCAGTGT      4020

TAAAATTTTA GTAGGTCCGC TAGCAGTACT AATCATGTGA GGAAATGATG AGAAATATTA      4080

AATTGGGAAA ACTCCATCAA TAAATGTTGC AATGCATGAT AAAAAAAA                  4129
```